(12) United States Patent
Bodewes et al.

(10) Patent No.: US 10,898,106 B2
(45) Date of Patent: Jan. 26, 2021

(54) IMPLANTABLE KNEE SENSOR AND METHODS OF USE

(71) Applicant: Biomet Manufacturing, LLC, Warsaw, IN (US)

(72) Inventors: Hilbrandus H. Bodewes, Delfgauw (NL); Mohammed Imran Khan, Berkshire (GB); Daniel László-Deli, Dordrecht (NL); Max Hoeboer, Dordrecht (NL); Lisa Abdel Alim-van den Berg, Dordrecht (NL); Siemon Van Opstal, Dordrecht (NL); Bonita Koperdraat, Dordrecht (NL); Bart Krijgsman, Dordrecht (NL); Jurrit Heerink, Dordrecht (NL)

(73) Assignee: Biomet Manufacturing, LLC, Warsaw, IN (US)

( * ) Notice: Subject to any disclaimer, the term of this patent is extended or adjusted under 35 U.S.C. 154(b) by 837 days.

(21) Appl. No.: 15/399,131

(22) Filed: Jan. 5, 2017

(65) Prior Publication Data
US 2018/0184944 A1    Jul. 5, 2018

(51) Int. Cl.
*A61B 5/01* (2006.01)
*A61B 5/1459* (2006.01)
(Continued)

(52) U.S. Cl.
CPC ........... *A61B 5/076* (2013.01); *A61B 5/0031* (2013.01); *A61B 5/01* (2013.01); *A61B 5/1459* (2013.01);
(Continued)

(58) Field of Classification Search
CPC ......... A61B 5/076; A61B 5/0031; A61B 5/01; A61B 5/14532; A61B 5/14539;
(Continued)

(56) References Cited

U.S. PATENT DOCUMENTS

| | | |
|---|---|---|
| 5,197,488 A | 3/1993 | Kovacevic |
| 5,425,775 A | 6/1995 | Kovacevic et al. |

(Continued)

FOREIGN PATENT DOCUMENTS

| | | |
|---|---|---|
| CA | 2990816 | 12/2015 |
| EP | 2967879 | 1/2016 |

(Continued)

OTHER PUBLICATIONS

D'Lima, Darryl D., et al., "Implantable sensor technology: measuring bone and joint biomechanics of daily life in vivo", Arthritis Research & Therapy 15:203, (2013), p. 1-8.

(Continued)

*Primary Examiner* — Navin Natnithithadha
(74) *Attorney, Agent, or Firm* — Schwegman Lundberg & Woessner, P.A.

(57) ABSTRACT

An implantable sensor configured to be inserted in an intramedullary canal can include a primary insert, a secondary insert, and an antenna. The primary insert can include a distal end, a proximal end opposite the distal end, and a central bore that can extend from an opening in the distal end towards the proximal end. A secondary insert can be receivable within the central bore through the opening. The secondary insert can include a body and a sensor module. The body can be removably engageable with an inside surface of the central bore. The sensor module can be disposable within the body and can be configured to produce a sensor signal as a function of a first sensed parameter indicative of infection. The antenna can be disposed in the central bore. The antenna can be configured to transmit a wireless signal as a function of the sensor signal.

15 Claims, 14 Drawing Sheets

(51) Int. Cl.
*A61B 5/07* (2006.01)
*A61F 2/38* (2006.01)
*A61B 5/145* (2006.01)
*A61B 5/1455* (2006.01)
*A61B 5/00* (2006.01)
*A61F 2/30* (2006.01)

(52) U.S. Cl.
CPC ...... *A61B 5/14532* (2013.01); *A61B 5/14539* (2013.01); *A61B 5/14551* (2013.01); *A61B 5/4504* (2013.01); *A61B 5/4528* (2013.01); *A61B 5/6878* (2013.01); *A61B 5/0008* (2013.01); *A61B 2560/0219* (2013.01); *A61F 2/30721* (2013.01); *A61F 2/38* (2013.01); *A61F 2002/30668* (2013.01); *A61F 2002/30878* (2013.01)

(58) Field of Classification Search
CPC . A61B 5/14551; A61B 5/1459; A61B 5/4504; A61B 5/4528; A61B 5/6878; A61B 5/0008; A61B 2560/0219; A61F 2/30721; A61F 2/38; A61F 2002/30668; A61F 2002/30878
USPC .......................................................... 600/302
See application file for complete search history.

(56) References Cited

U.S. PATENT DOCUMENTS

| | | | |
|---|---|---|---|
| 6,034,296 A | 3/2000 | Elvin et al. | |
| 6,245,109 B1 | 6/2001 | Mendes et al. | |
| 6,447,448 B1 | 9/2002 | Ishikawa et al. | |
| 6,610,096 B2 | 8/2003 | MacDonald | |
| 6,821,299 B2 | 11/2004 | Kirking et al. | |
| 7,097,662 B2 | 8/2006 | Evans, III et al. | |
| 7,190,273 B2 | 3/2007 | Liao et al. | |
| 7,218,232 B2 * | 5/2007 | DiSilvestro | A61B 90/98 340/572.8 |
| 7,256,695 B2 * | 8/2007 | Hamel | G06K 7/10316 340/572.1 |
| 7,328,131 B2 | 2/2008 | Donofrio et al. | |
| 7,384,403 B2 | 6/2008 | Sherman | |
| 7,470,288 B2 | 12/2008 | Dietz et al. | |
| 7,478,108 B2 * | 1/2009 | Townsend | G08B 21/0446 |
| 7,668,667 B2 * | 2/2010 | Robb | G01N 29/043 702/35 |
| 7,786,867 B2 * | 8/2010 | Hamel | G06K 19/0723 340/572.1 |
| 7,970,734 B2 * | 6/2011 | Townsend | G08B 21/0453 707/602 |
| 8,029,566 B2 | 10/2011 | Lozier et al. | |
| 8,032,486 B2 * | 10/2011 | Townsend | G08B 21/0453 707/602 |
| 8,080,064 B2 | 12/2011 | Dietz et al. | |
| 8,176,922 B2 * | 5/2012 | Sherman | A61F 2/38 128/899 |
| 8,241,296 B2 | 8/2012 | Wasielewski | |
| 8,486,070 B2 | 7/2013 | Morgan et al. | |
| 8,502,675 B2 * | 8/2013 | Hamel | H04Q 9/00 340/572.4 |
| 8,720,270 B2 | 5/2014 | Stein et al. | |
| 8,956,418 B2 | 2/2015 | Wasielewski et al. | |
| 9,301,720 B2 | 4/2016 | Stein | |
| 9,357,964 B2 | 6/2016 | Stein et al. | |
| 9,532,730 B2 | 1/2017 | Wasielewski | |
| 9,629,583 B2 | 4/2017 | Gradel et al. | |
| 10,499,855 B2 | 12/2019 | Hunter | |
| 10,524,694 B2 | 1/2020 | Hunter | |
| 2002/0024450 A1 * | 2/2002 | Townsend | G08B 21/0453 340/870.16 |
| 2004/0019384 A1 * | 1/2004 | Kirking | A61B 5/076 623/20.14 |
| 2005/0012610 A1 | 1/2005 | Liao et al. | |
| 2006/0009856 A1 * | 1/2006 | Sherman | A61B 5/0031 623/20.32 |
| 2006/0047283 A1 | 3/2006 | Evans, III et al. | |
| 2007/0005141 A1 * | 1/2007 | Sherman | A61B 5/0031 623/18.12 |
| 2007/0179627 A1 * | 8/2007 | Gustilo | A61F 2/30734 623/20.15 |
| 2007/0233267 A1 | 10/2007 | Amirouche et al. | |
| 2007/0239282 A1 * | 10/2007 | Caylor, III | G06F 19/3481 623/20.34 |
| 2009/0005708 A1 | 1/2009 | Johanson et al. | |
| 2009/0005876 A1 | 1/2009 | Dietz et al. | |
| 2009/0112523 A1 * | 4/2009 | Townsend | G08B 21/0453 702/187 |
| 2010/0165593 A1 * | 7/2010 | Townsend | G08B 21/0453 361/807 |
| 2010/0331633 A1 | 12/2010 | Stein | |
| 2011/0004076 A1 | 1/2011 | Janna et al. | |
| 2016/0029952 A1 | 2/2016 | Hunter et al. | |
| 2016/0310077 A1 | 10/2016 | Hunter et al. | |
| 2017/0189553 A1 | 7/2017 | Hunter | |
| 2017/0348106 A1 | 12/2017 | Zarling et al. | |
| 2018/0125366 A1 | 5/2018 | Lucey et al. | |
| 2020/0069247 A1 | 3/2020 | Hunter | |

FOREIGN PATENT DOCUMENTS

| | | |
|---|---|---|
| EP | 2967926 | 1/2016 |
| EP | 3160331 | 5/2017 |
| JP | 2019217337 | 12/2019 |

OTHER PUBLICATIONS

D'Lima, Darryl D., "In vivo tibial force measurement after total knee arthroplasty", UC San Diego Electronic Theses and Dissertations, (2007), 103 pgs.
"European Application Serial No. 18150245.1, Extended European Search Report dated Jun. 7, 2018", 8 pgs.
"European Application Serial No. 18150245.1, Response Filed Jan. 11, 2019 to Extended European Search Report dated Jun. 7, 2018", 15 pgs.

* cited by examiner

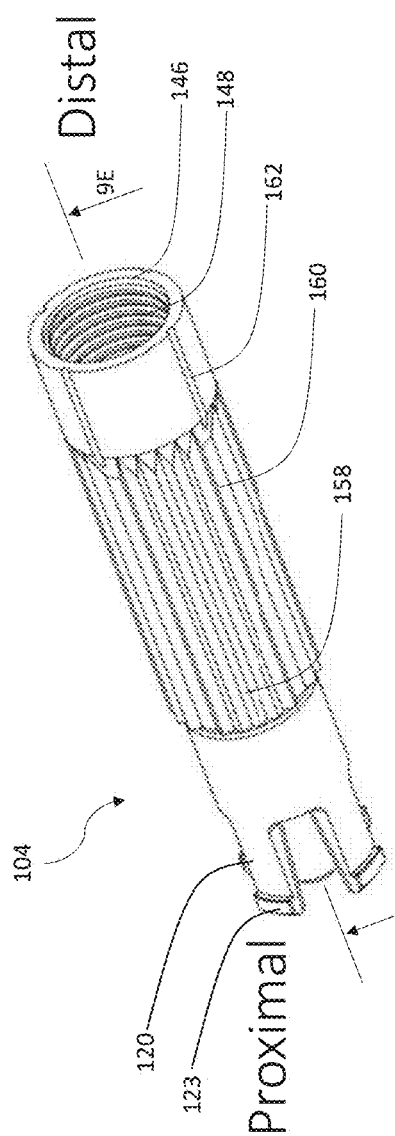
FIG. 9A
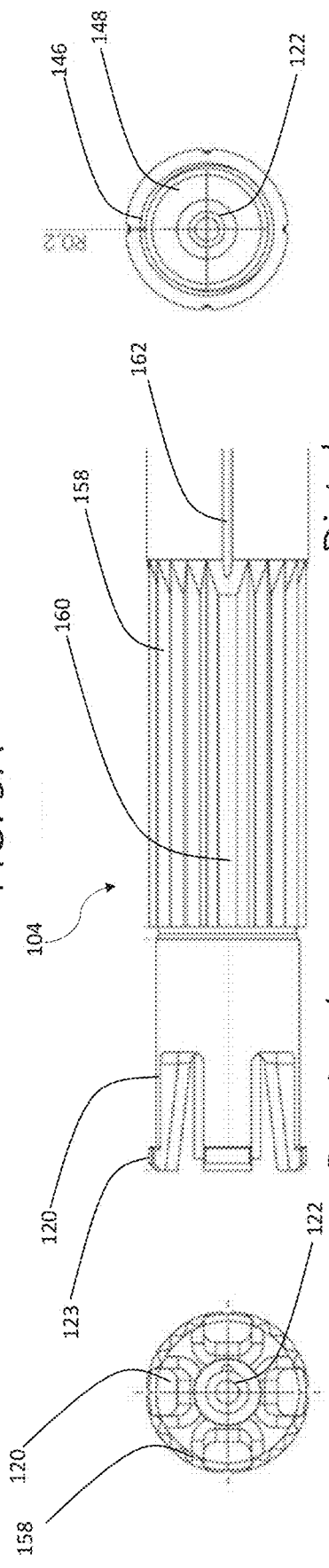
FIG. 9B
FIG. 9D
FIG. 9C

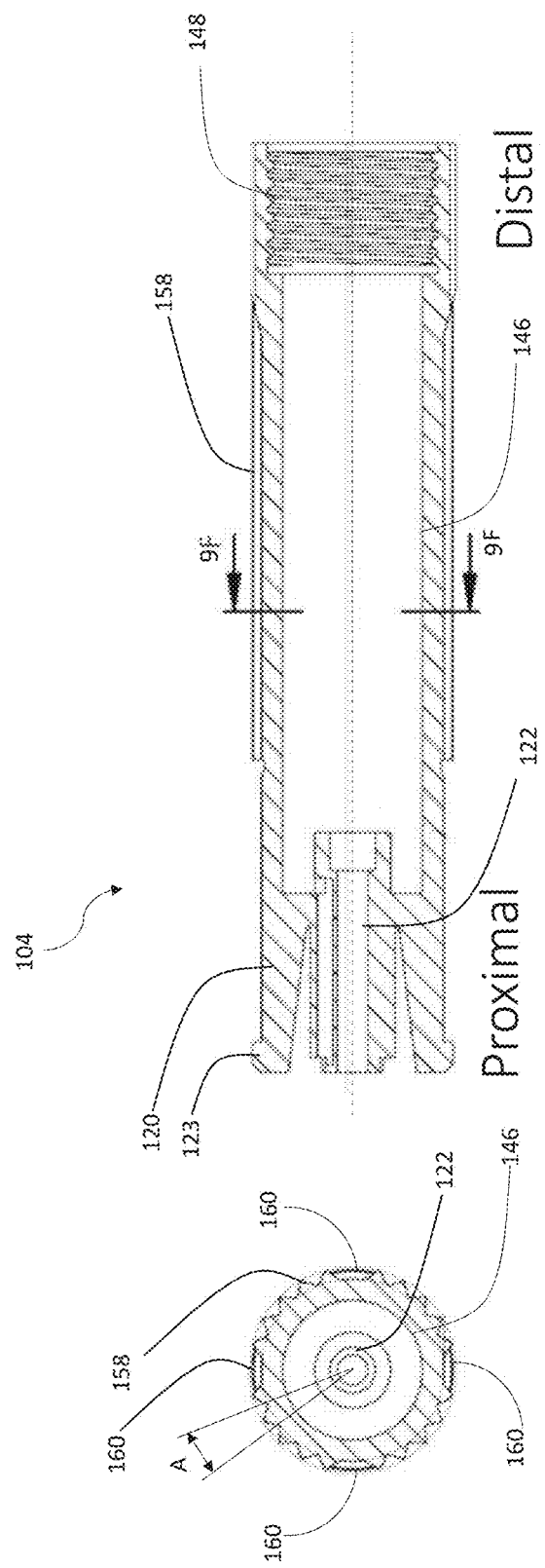

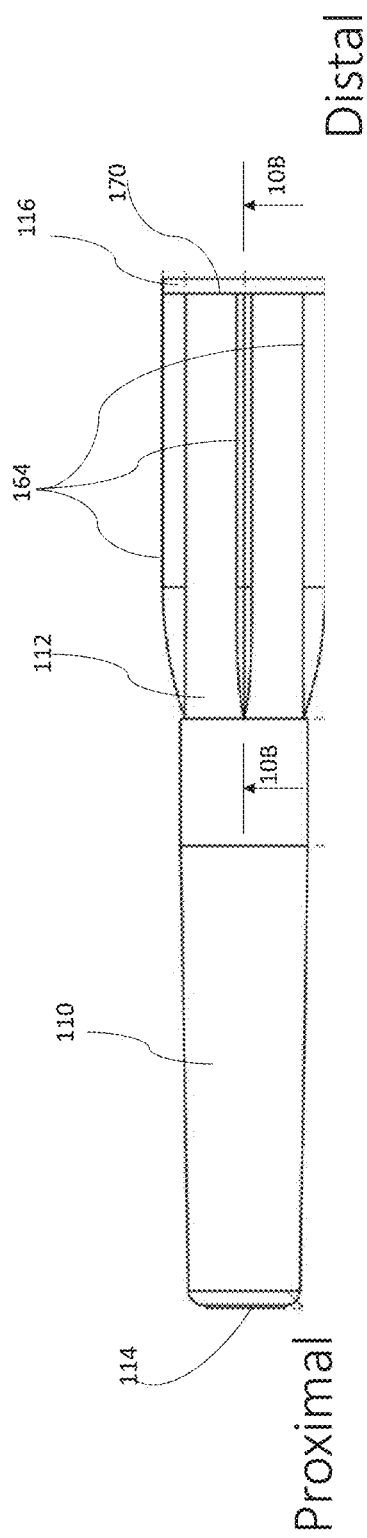
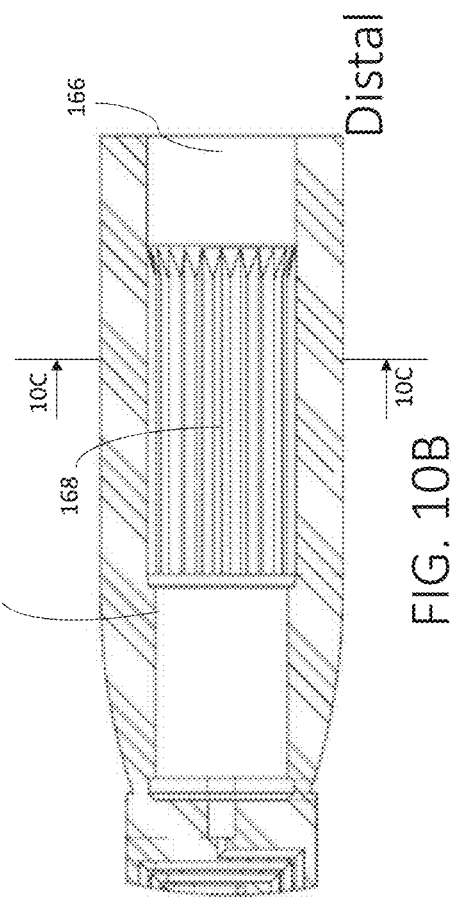
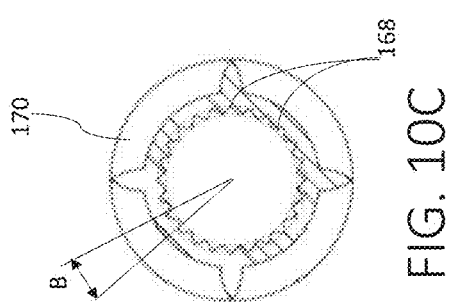
FIG. 10A
FIG. 10B
FIG. 10C

IMPLANTABLE KNEE SENSOR AND METHODS OF USE

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components. During orthopedic procedures, such as knee replacement or similar joint reconstruction surgeries, various prostheses can be used in the various procedures, including implant prostheses including sensors.

OVERVIEW

Assemblies, configurations, and methods of use for an implantable sensor module can be useful for early detection of infection. In an example, the implantable sensor provides a convenient, compact, and self-contained module that can be inserted into an already required cavity for various knee reconstruction surgeries. The implantable sensor module can be a passive sensor that is wirelessly activated and powered, such as through NFC, and wirelessly communicates with an external computing device to provide sensed information regarding the environment surrounding a prosthetic implant. The external computing device and other devices connected thereto can perform complex calculations, render graphical interfaces, and store data information related to data provided by the implantable sensor, providing significant means for detection of an infection.

The present inventors have recognized, among other things, the current surgical techniques, and surgeries in general, for joint reconstruction and other similar procedures can result in an infection around the installed prosthetic. These problems, and others, are addressed by the present invention through the ability to install a sensor module into the joint of a patient. An installed sensor that can communicate with an external device the existing conditions within a body of a patient in and around a prosthesis can offer a benefit of early detection of infection. Early detection of infection can reduce further required procedures, such as revisions, saving cost and providing improved quality of life. Additional benefits arising from the present subject matter will be obvious to one of ordinary skill in the art when reading the remainder of the detailed description.

The following, non-limiting examples, detail certain aspects of the present subject matter to solve the challenges and provide the benefits discussed herein, among others.

Example 1 is an implantable sensor configured to be inserted in an intramedullary canal, the implantable sensor comprising: a primary insert including a distal end, a proximal end opposite the distal end, and a central bore extending from an opening in the distal end towards the proximal end; a secondary insert receivable within the central bore through the opening, the secondary insert comprising: a body removably engageable with an inside surface of the central bore; and a sensor module disposable within the body and configured to produce a sensor signal as a function of a first sensed parameter indicative of infection; and an antenna disposed in the central bore, the antenna configured to: transmit a wireless signal as a function of the sensor signal.

In Example 2, the subject matter of Example 1 optionally includes wherein the sensor comprises one of a temperature sensor, a pH sensor, an oxygen sensor, a carbon dioxide sensor, and a glucose sensor.

In Example 3, the subject matter of any one or more of Examples 1-2 optionally include wherein the antenna is configured to receive power from an external source and distribute the power to the sensor.

In Example 4, the subject matter of any one or more of Examples 1-3 optionally include wherein the secondary insert further comprises: a cap releasably securable to the secondary insert.

In Example 5, the subject matter of Example 4 optionally includes wherein the cap and sensor module are releasable from the secondary insert while the secondary insert is inserted in the intramedullary canal.

In Example 6, the subject matter of any one or more of Examples 4-5 optionally include wherein the cap further comprises: a plurality of legs projecting proximally from a proximal surface of the cap and configured to retain the sensor capsule.

In Example 7, the subject matter of any one or more of Examples 1-6 optionally include wherein the secondary insert further comprises: a second sensor configured to produce a second sensor signal as a function of a second sensed parameter indicative of infection.

In Example 8, the subject matter of Example 7 optionally includes wherein the secondary insert further comprises: a third sensor configured to produce a third sensor signal as a function of a third sensed parameter indicative of infection.

In Example 9, the subject matter of any one or more of Examples 1-8 optionally include wherein the secondary insert further comprises: an optical fiber connected to the sensor and extending through a periphery of the secondary insert to expose the optical fiber to a joint cavity adjacent to the intramedullary canal to send an optical signal to the sensor as a function of sensed optical conditions of the joint cavity.

In Example 10, the subject matter of Example 9 optionally includes a cap releasably securable to the secondary insert, the cap comprising: a passage exposing the sensor module to the joint cavity, the passage receivable of the optical fiber.

In Example 11, the subject matter of any one or more of Examples 1-10 optionally include wherein the central bore further comprises a plurality of grooves extending axially along a surface of the central bore, and wherein the secondary insert further comprises a plurality of ribs projecting radially outward from an outer surface of the secondary insert and extending axially along the outer surface, the plurality of ribs mateable with the plurality of grooves to prevent rotation of the secondary insert relative to the primary insert.

Example 12 is a system for monitoring a joint cavity, the system comprising: an implantable sensor comprising: a femoral insert implantable in a femoral intramedullary canal adjacent to the joint cavity, the femoral insert comprising: a proximal end and a distal end; and a central bore extending from the distal end through the distal portion and terminating prior to the proximal end; a sensor insertable into the central bore through the distal end, the sensor configured to produce a sensor signal as a function of a sensed condition of the joint cavity; and an antenna disposed in the central bore, the antenna configured to: transmit a wireless signal as a function of the sensor signal; and receive power and distribute the power to the sensor.

In Example 13, the subject matter of Example 12 optionally includes a central device in communication with the external computing device, the central device configured to analyze data received from the external computing device and return analysis to the external computing device.

In Example 14, the subject matter of Example 13 optionally includes an expert device in communication with at least one of the external computing device and the central device, the expert device configured to: analyze data received from at least one of the external computing device the central device; and analyze analysis received from the central device.

In Example 15, the subject matter of any one or more of Examples 12-14 optionally include wherein the secondary insert further comprises: a communication chip connected to the antenna and the sensor, the communication chip configured to process the sensor signal and distribute power from the antenna to the sensor.

In Example 16, the subject matter of Example 15 optionally includes wherein the communication chip comprises a near field communication chip.

Example 17 is an intramedullary implant configured to be inserted in a femoral intramedullary canal, the intramedullary implant comprising: a housing insertable into a femoral intramedullary canal, the housing comprising: a proximal portion including a proximal end; a distal portion including a distal end; and a bore extending from the distal end towards the proximal end; a secondary insert receivable in the bore, the secondary insert engageable with an internal surface of the bore, and including a sensor configured to produce a sensor signal as function of a first sensed parameter of a joint cavity adjacent the intramedullary canal, the first sensed parameter indicative of infection; and an antenna coil disposed in the proximal portion, the antenna configured to transmit a wireless signal as a function of the sensor signal.

In Example 18, the subject matter of Example 17 optionally includes wherein the secondary insert comprises a snap fit connection securable to the central bore.

In Example 19, the subject matter of Example 18 optionally includes wherein the snap fit connection comprises a plurality of straight arms, each arm of the plurality of arms including a projection extending radially from a proximal termination of each arm.

In Example 20, the subject matter of any one or more of Examples 17-19 optionally include wherein the antenna coil is positionable within the proximal portion to change a coil angle relative to the sensor module.

In Example 21, the subject matter of any one or more of Examples 1-11 optionally include wherein primary insert is comprised of PEEK.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9A illustrates an isometric view of a secondary insert of an implantable sensor, in accordance with at least one example of this disclosure.

FIG. 9B illustrates a plan view of a secondary insert of an implantable sensor, in accordance with at least one example of this disclosure.

FIG. 9C illustrates an end view of a secondary insert of an implantable sensor from a proximal perspective, in accordance with at least one example of this disclosure.

FIG. 9D illustrates an end view of a secondary insert of an implantable sensor from a distal perspective, in accordance with at least one example of this disclosure.

FIG. 9E illustrates a cross-section view of an implantable sensor across indicators 9E-9E of FIG. 9A, in accordance with at least one example of this disclosure.

FIG. 9F illustrates a cross-section view of an implantable sensor across indicators 9F-9F of FIG. 9E, in accordance with at least one example of this disclosure.

FIG. 10A illustrates a plan view of an implantable sensor, in accordance with at least one example of this disclosure.

FIG. 10B illustrates a cross-section view of an implantable sensor across indicators 10B-10B of FIG. 10A, in accordance with at least one example of this disclosure.

FIG. 10C illustrates a cross-section view of an implantable sensor across indicators 10C-10C of FIG. 10B, in accordance with at least one example of this disclosure.

DETAILED DESCRIPTION

Detailed structure, configurations, and methods of use for an implantable knee sensor are generally disclosed herein. In one example, an implantable sensor includes a primary insert, secondary insert, an antenna, and a sensor. For example, during total knee arthroplasty (TKA), a surgeon can install an implantable sensor in an intramedullary femoral cavity including a sensor that can be configured to detect conditions indicative of infection. The antenna can then broadcast a signal containing data produced as a function of the sensed conditions.

Figure 1:
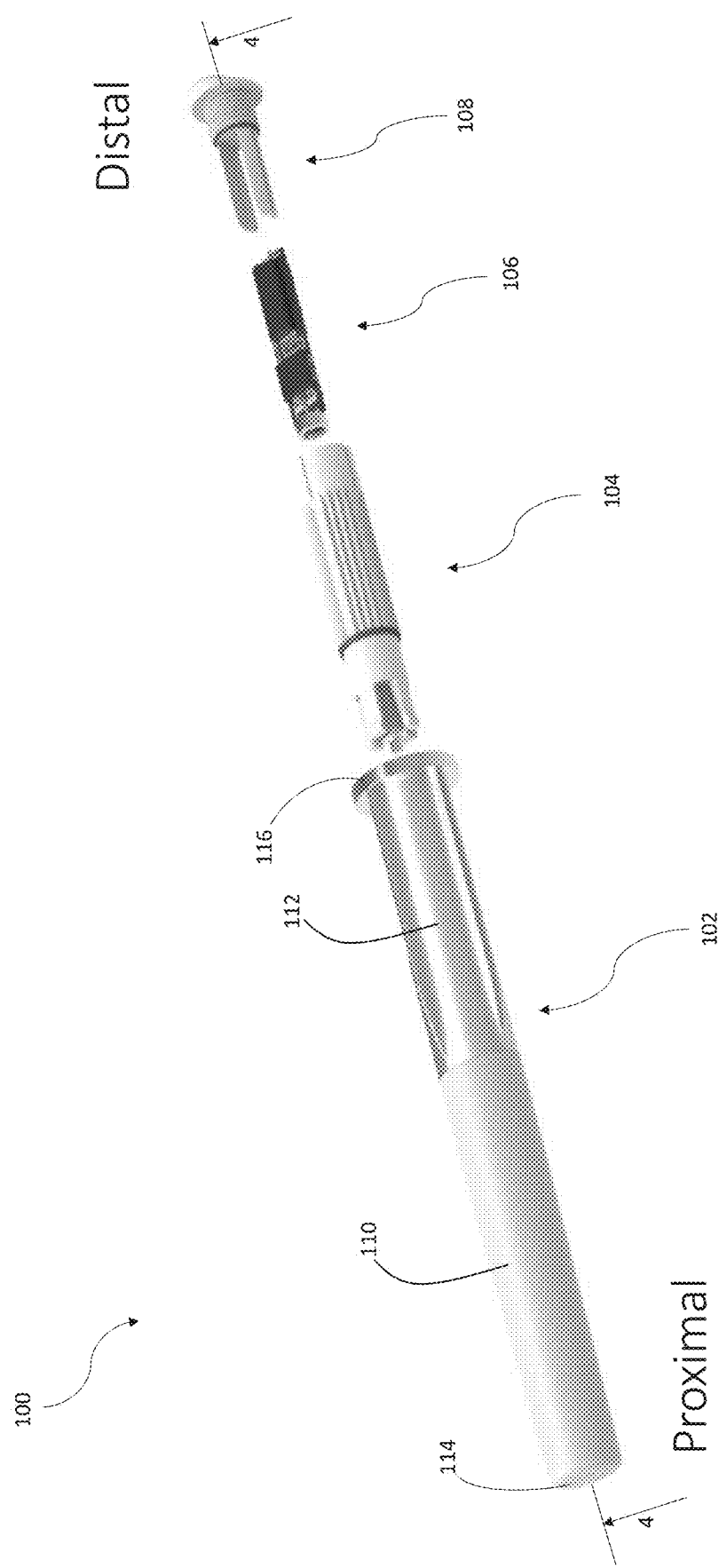
FIG. 1 illustrates a three dimensional exploded view of an implantable sensor, in accordance with at least one example of this disclosure.

FIG. 1 illustrates a three dimensional exploded view of implantable sensor 100, in accordance with at least one example of this disclosure. Implantable sensor 100 can include primary insert 102 and secondary insert 104. Secondary insert 104 can include sensor module 106, and cap 108. Primary insert can include proximal portion 110, distal portion 112, proximal end 114, and distal end 116.

Primary insert 102, or femoral fixation unit (FFU), can be an elongate member, such as a tubular member, having a generally tapered cylindrical shape, including a flange at distal end 116. Distal portion 112 can be press fit into proximal portion 110, such that distal portion 112 has a pin or insertion portion that is similar in size to, or slightly larger than, a bore within the proximal portion 110. For example, the pin portion and the bore can be about 5 millimeters to 15 millimeters in some examples, and about 8 millimeters to 10 millimeters some examples, with an interference of −0.5 to 0.5 millimeters in some examples.

Primary insert 102 can be comprised of a suitable metal, polymer, and the like, for insertion into a bone of a human body, such as steel, cobalt, titanium, polyether ether ketone (PEEK). In one example, primary insert 102 can be comprised of PEEK and coated with titanium and/or a hydroxyapatite coating. Secondary insert 104 and cap 108 can be comprised of similar materials. This can provide the benefit of reducing signal attenuation of signal while accepting coatings enabling fixation.

Secondary insert 104 can be a generally tubular body having a snap connection at a proximal end and an opening at a distal end. Secondary insert 104 can be inserted and secured within distal portion 112 of primary insert 110.

Sensor module 106 can include one or more sensors, a communication chip, and a processor, as discussed further below. Sensor module 106 can be coupled to cap 108 and inserted into secondary insert 104. Sensor module 106 can be electrically connected to an antenna enclosed within proximal portion 110 of primary insert 102. Cap 108 can include a threaded portion configured to releasably secure to a threaded portion of distal portion 112, securing sensor module 106 within secondary insert, and axially securing secondary insert 104 within distal portion 112. Cap 108 can be removed during, for example, follow-up procedures such as to revise or replace components of implantable sensor 100. However, cap 108 can be securable to distal portion 112 such that cap 108 will not become separated from senor module 106 under normal conditions of use while implanted. In some other examples, cap 108 can engage sensor module 106 so that cap 108 is not removable from sensor module 106, which can protect sensor module 106, helping to prevent exposure of electronic components to bodily fluids.

Figure 2:
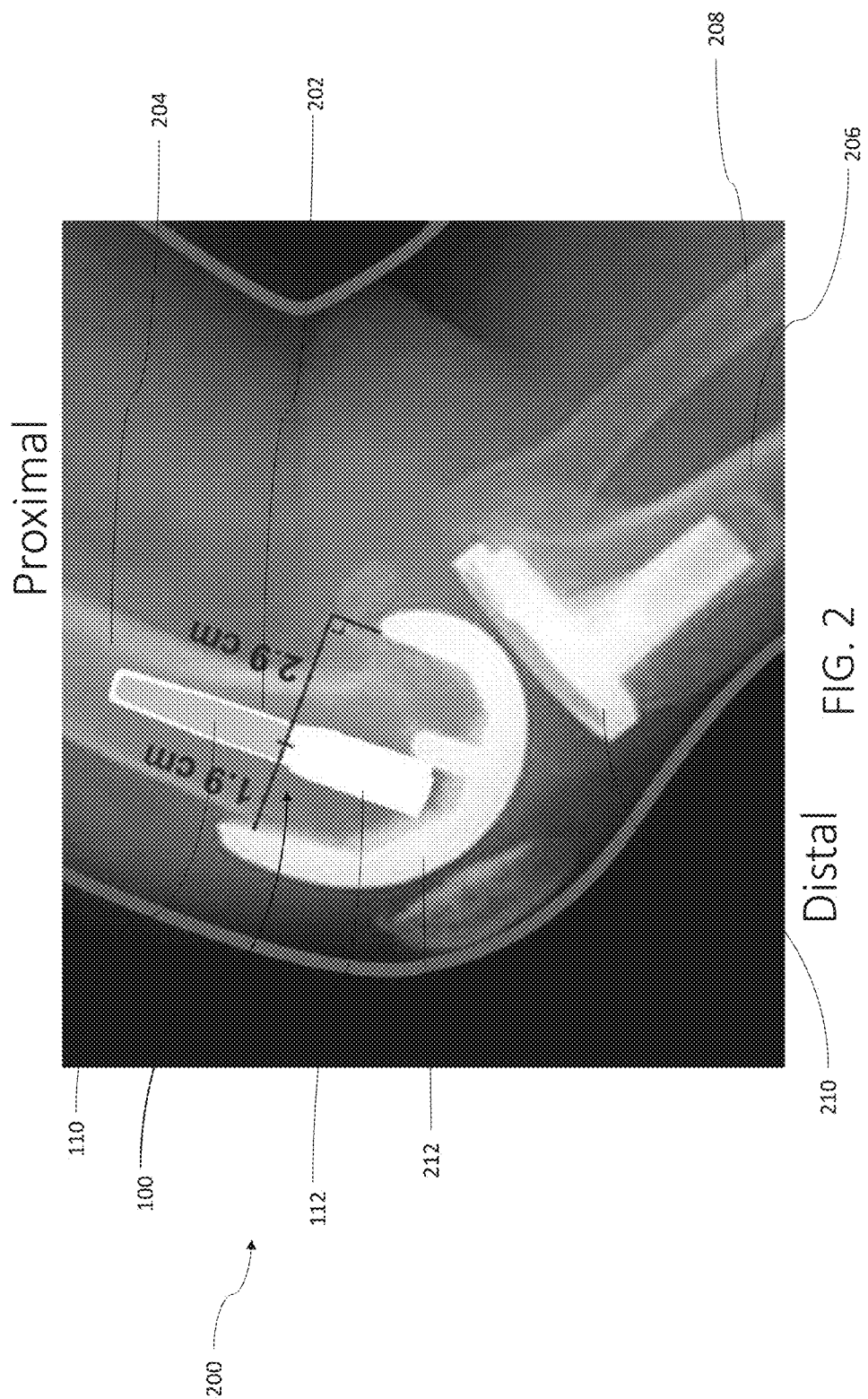
FIG. 2 illustrates an adapted, illustrative X-ray image of an implantable sensor installed in a femoral intramedullary canal, in accordance with at least one example of this disclosure.

FIG. 2 illustrates an adapted, illustrative X-ray image image of implantable sensor 100 installed in femoral intramedullary canal 202 of femur 204, in accordance with at least one example of this disclosure. FIG. 2 also shows proximal portion 110 and distal portion 112 of implantable sensor 100. Also shown in FIG. 1 are tibia 206, fibula 208, tibial implant 210, and femoral implant 212.

The components of FIG. 2 can be consistent with those of a total knee arthroplasty or knee revision procedure, where orthopedic procedures and prostheses can be utilized to repair and/or replace damaged bone and tissue in a human body. In some examples, such as the example of FIG. 2, prostheses can be used to replicate articular knee surfaces. Knee prostheses can include tibial implant 210 inserted into through a resected proximal surface of tibia 206 and into fibula 206. Femoral implant 212 can be implanted on and secured to a distal end of femur 204. Femoral implant 212 can articulate with a tibial bearing component on the proximal end of tibial implant 210 implanted to replicate the function of a healthy natural knee.

During some types of arthroplasties, a bore can be drilled into the distal end of femur 204. The bore can be sized to receive surgical tools, such as cutting guides. The bore can also be used to secure femoral implant 212 to femur 203 using a fastener, such as a screw. This process can create or expand intramedullary canal 202. After installation of femoral implant 212 onto femur 204 in the prior art, intramedullary canal 202 can be filled, can receive a fastener, or can be left empty for use in future procedures. The present disclosure offers the benefit of making use of a cavity already required by some arthroplasty procedures, by providing implantable sensor 100, which can be configured for installation within intramedullary canal 202.

Implantable sensor 100 can be sized to secure to intramedullary canal 202 in a press fit configuration. For example, implantable sensor 100 can have an outside diameter that is similar to or slightly larger than an inside diameter of intramedullary canal 202. Additionally, implantable sensor 100 can have a length (in an axial direction of implantable sensor 100) such that implantable sensor 100 does not interfere with femoral implant 212, and such that cap 108 (of FIG. 1) is exposed (as discussed below). Implantable sensor 100 can be additionally secured to femur 204 using an adhesive, such as polymethylmethacrylate (PMMA).

In some examples, implantable sensor 100 can be secured within intramedullary canal 202 disposed through femoral implant 212, but not connected or secured thereto. This can enable removal of implantable sensor 100 without removing femoral implant 212. In some examples, implantable sensor 100 can be mechanically interconnected (upon implantation) with the femoral implant. In some examples, implantable sensor 100 can be secured to femoral implant 212 using a peg, pin, screw, and the like, to help prevent axial motion of implantable sensor relative to intramedullary canal 202.

Figure 3:
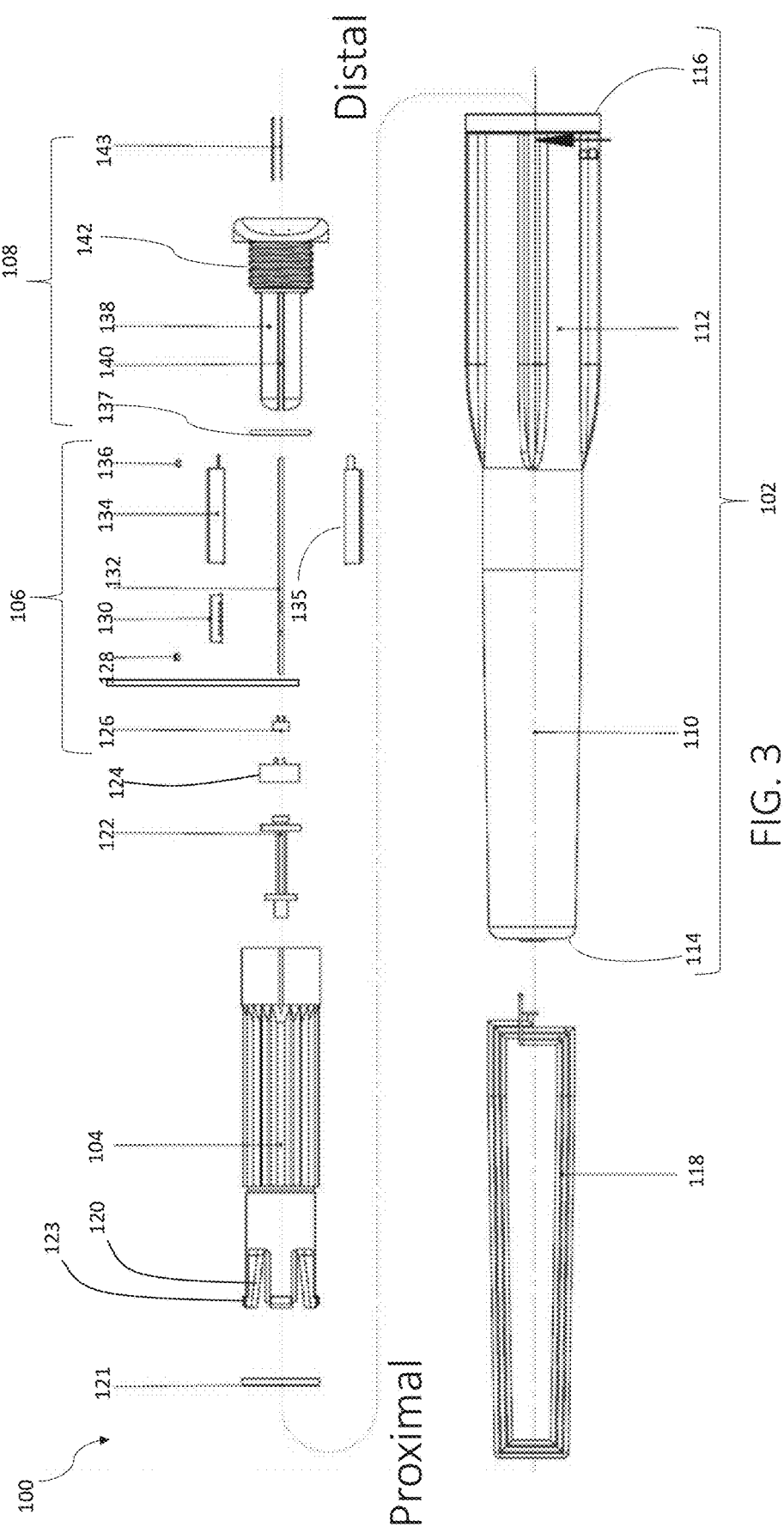
FIG. 3 illustrates an exploded view of an implantable sensor, in accordance with at least one example of this disclosure.
Figure 4:
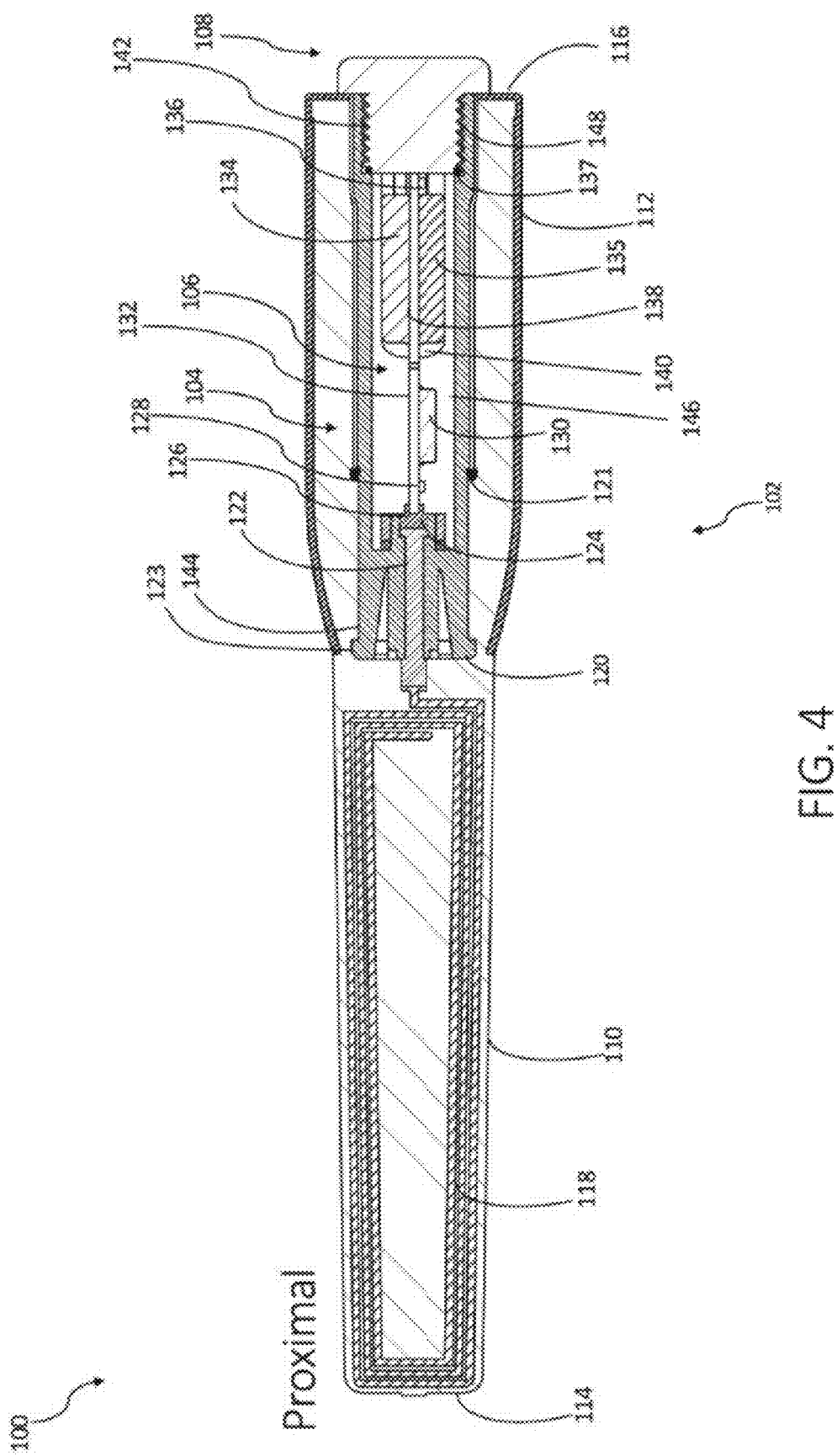
FIG. 4 illustrates cross-sectional view of an implantable sensor across indicators 4-4 of FIG. 1, in accordance with at least one example of this disclosure.

FIG. 3 illustrates an exploded view of implantable sensor 100, in accordance with at least one example of this disclosure. FIG. 4 illustrates a cross-sectional view of implantable sensor 100 across indicators 4-4 of FIG. 1, in accordance with at least one example of this disclosure. FIGS. 3 and 4 are discussed concurrently.

Implantable sensor 100 can include primary insert 102 and secondary insert 104. Secondary insert 104 can include sensor module 106, cap 108, and antenna coil 118. Primary insert can include proximal portion 110, distal portion 112, proximal end 114, and distal end 116. Secondary insert can include snap fits 120, outer ring 121, coil connector 122, projections 123, and outer connector 124. Sensor module 106 can include inner connector 126, capacitor 128, communication chip 130, printed circuit board (PCB) 132, first sensor 134, second sensor 135, and third sensor 136. Cap 108 can include inner ring 137, arms 138, PCB slots 140, threaded portion 142, and optical fibers 143 (FIG. 3). Primary insert 102 can also include central bore 144 (FIG. 4). Secondary insert 104 can also include secondary insert bore 146 (FIG. 4) and internal threaded portion 148 (FIG. 4)

Antenna coil 118 can be a coil type antenna in some examples, configured to be disposed in proximal portion 110 and connected to coil connector 122. Coil connector can connect to outer connector 124, thus electrically connecting sensor module 106 to antenna coil 118. Coil connector 122, outer connector 124, and inner connector 126 can be comprised of biocompatible materials that are conductive, such as titanium, steel, silver, and the like. Because secondary insert 104 can be placed in primary insert at several positions (as described below), and antenna coil 118 can be placed within proximal portion 110 at varying angles (also described below), coil connector 122 can be configured to connect antenna coil 118 to sensor module 106 at a variety of angles.

Central bore 144 can be a bore beginning at distal end 116 and extending through distal portion 112 and proximal portion 110, terminating in proximal portion 110 prior to proximal end 114. In some examples, central bore 144 can have a diameter in proximal portion 110 that is larger than a second diameter in distal portion 112.

Secondary insert 104 can be disposed within central bore 144 within distal portion 112 of primary insert 102, such that secondary insert extends from distal end 116 through distal portion 112, terminating at proximal portion 110. Outer ring 121 can be disposed around an outer surface of secondary insert 104 to form a seal in central bore 144. In some examples, outer ring 121 of secondary insert 104 can be a seal such as an o-ring or other type of annular seal.

Snap fits 120 of secondary insert 104, can be disposed at the proximal termination of secondary insert 104. Snap fits 120 can each include projections 123, which can extend radially from a proximal termination of snap fits 120. Projections 123 can be sized to have a larger diameter than that of central bore 144, so that when secondary insert 104 is inserted into central bore 144, central bore 144 can force projections 123 radially inward, allowing secondary insert 104 to be moved through central bore 144 axially towards proximal end 114. As secondary insert 104 moves further into central bore 144, projections 123 can expand when projections 123 reach a section of central bore 144 having a larger diameter, such as an undercut or counter bore. After expanding, projections 123 can engage the undercut or other surface of central bore 144 after projections 123 and snap fits 120 expand to their original diameter.

In some examples, the engagement of snap fits 120 with a portion of central bore 144 can prevent secondary insert from moving axially towards distal end 116. In some examples, projections 123 can be sized to be as small as possible, to minimize a wall thickness of primary insert 102. In some examples, snap fits 120 can include a quantity of snap fits 120 designed to reduce stress in snap fits 120 during installation (compression and expansion of snap fits 120) of secondary insert 104 in central bore 144. In some examples, a quantity of snap fits 120 can be 1, 2, 3, 4, 5, or 6, and the like. In some examples, snap fits 120 can include a geometry designed to reduce stress in snap fits 120 during installation, such as a tapered rectangular extension including a radially extending projection, for example.

Sensor module 106 includes PCB 132, which can be a printed circuit board configured to support and electrically connect the components of sensor module 106. As discussed above, internal connector 126 connects to external connector 124, which connects to coil connector 122. Internal connector 126 is also electrically connected to PCB 132 at a proximal end of PCB 132.

Capacitor 128, communication chip 130, first sensor 134, second sensor 135, and third sensor 136 can also be electrically connected to PCB 132 and supported by PCB 132. First sensor 134, second sensor 135, and third sensor 136 can be connected to optical fibers 143 to place first sensor 134 and/or second sensor 135 and/or third sensor 136 in communication with an environment outside of sensor implant 100, such as synovial fluid that can be found in a distal portion of femur 204. First sensor 134, second sensor 135, and third sensor 136 can be electrochemical, amperometric, potentiometric, conduct metric, thermometric, optical, luminescent, such as sensor configured to produce a signal as a function of glucose, temperature, oxygen (O2), carbon dioxide (CO2), or Ph. In one example, an optical sensor can be configured to convert an optical signal into a sensor signal that is a function of a measured optical condition, as discussed further below.

Cap 108 can be releasably securable to secondary insert 104, and in some examples can be releasably securable to secondary insert bore 146. In some examples, cap 108 can include threaded portion 142 having a diameter smaller than a distal portion of cap 108. Threaded portion 142 can extend towards proximal end 114. Secondary insert bore 146 can include internal threaded portion 148 configured to receive threaded portion 142 of cap 108. In some examples, inner ring 137 can be a seal such as an o-ring or other annular seal. In some examples, inner ring 137 can be configured to surround arms 138 and abut threaded portion 142 of cap 108 and internal threaded portion 148, creating a seal between cap 108 and secondary insert bore 146.

Arms 138 can extend axially in a generally proximal direction from a proximal surface of cap 108. Each of arms 138 can include PCB slots 140, which can be sized to receive and retain PCB 132. As discussed below, in some examples, arms 138 can be diametrically spaced to accommodate first sensor 134, second sensor 135, and third sensor 136 between arms 138. In some examples, cap 108 can be configured to receive optical fibers 143, which can connect to PCB 132 and/or first sensor 134 and/or second sensor 135 and/or third sensor 136, as discussed further below.

In operation of some examples, first sensor 134, second sensor 135, and third sensor 136 can be inactive (or passive) while installed in a patient. A physician or other user can then use an external device to transmit power to antenna coil 118 through induction of electromagnetic field powers. Antenna coil 118 can distribute the power to sensor module 106, and more specifically to communication chip 130. Communication chip 130 can distribute power to first sensor 134, second sensor 135, and third sensor 136, which can initiate their individual measurement sequences. The external device can then remain active, awaiting a return signal from antenna coil 118. Antenna coil 118 also can communicate through load modulation of an externally applied electromagnetic field.

In operation of some examples, optical fibers 143 can transmit to first sensor 134 and/or second sensor 135 and/or third sensor 136 an optical condition of the environment of a distal portion of femur 204, such as the joint cavity. The sensed condition can be converted and/or correlated to conditions of the environment such as temperature, Ph, and glucose by any of the sensors. First sensor 134 and/or second sensor 135 and/or third sensor 136 can produce sensor signals as a function of sensed conditions that can be transmitted from implantable sensor 100 to an external device (as described further below).

In some examples, glucose, Ph, and temperature can be used to detect conditions indicative of infection. For example, an elevated temperature can be indicative of the presence of an infection. In other examples, a deviation in glucose or Ph may indicate an infection. The external device can be configured to determine whether or not an infection exists in the sampled environment as a function of the signals received from implantable sensor 100. In addition, a combination of multiple sensors readings can provide a risk indication of local early infection, which can save cost and improve quality of a patient's life. Because sensor 100 is externally powered, sensor 100 does not require internal power, reducing the need for internal capacitors and power, which can have regulatory advantages.

Figure 5:
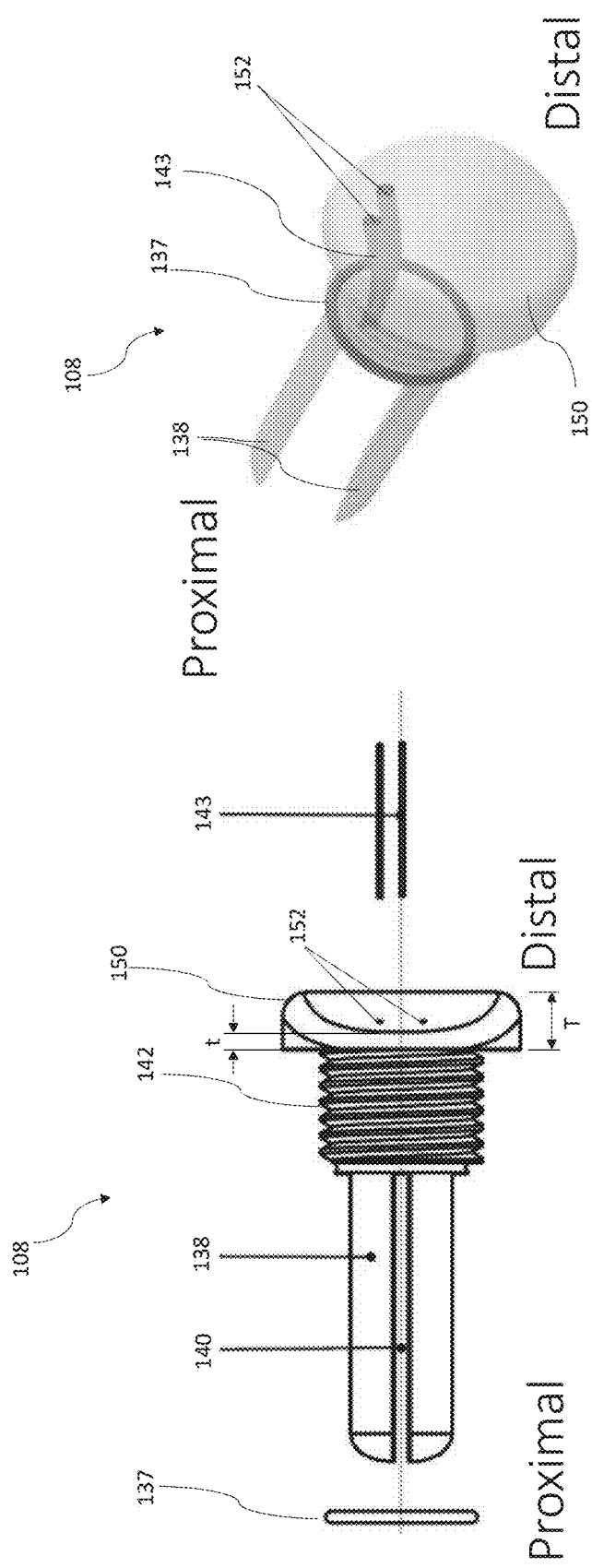
FIG. 5A illustrates a side view of a cap for an implantable sensor, in accordance with at least one example of this disclosure.
FIG. 5B illustrates an isometric view of a cap for an implantable sensor from a distal perspective, in accordance with at least one example of this disclosure.

FIG. 5A illustrates a side view of a cap for an implantable sensor, in accordance with at least one example of this disclosure. FIG. 5B illustrates an isometric view of a cap for a sensor module from a distal perspective, in accordance with at least one example of this disclosure. FIGS. 5A and 5B are discussed concurrently. FIGS. 5A and 5B show cap 108, which can include inner ring 137, arms 138, PCB slots 140, threaded portion 142, optical fibers 143, head portion 150, and passageways 152.

FIGS. 5A and 5B are consistent with FIGS. 1-4, but show further detail of cap 108, such as head portion 150, which has a diameter that is larger than threaded portion 142 and arms 138. Head portion 150 can include passageways 152, which can be bores, ports, and the like, passing through head portion 150 and part or all of threaded portion 142 to expose passageways 152 to a distal side of cap 108 and an internal portion of secondary insert 104.

Head portion can have a non-planar surface at a distal end, such that a thickness T of a portion of head portion 150 can be larger than a thickness t of another portion of head portion 150. In one example, ports 152 can be positioned at the portion of head portion 150 having thickness t, which can have the benefit of reducing a length of optical fibers 143.

Figure 6:
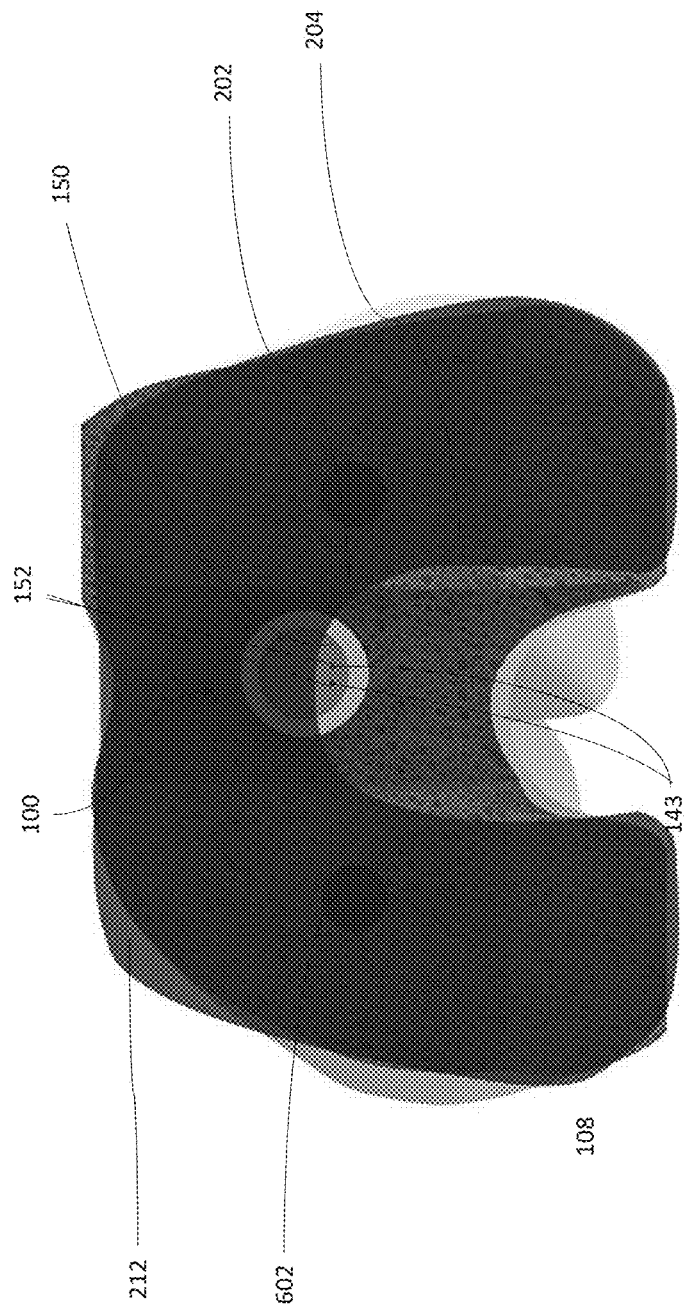
FIG. 6 illustrates an implantable sensor installed in a femoral intramedullary canal, in accordance with at least one example of this disclosure.

FIG. 6 illustrates implantable sensor 100 installed in femoral intramedullary canal 202 of femur 204, and surrounded by femoral implant 212. FIG. 6 shows cap 108, which can include optical fibers 143, head portion 150, and passageways 152. Cap 108 of implantable sensor 100, as shown in FIG. 6, can be connected and operate consistently with FIGS. 1-5. FIG. 6 further shows how cap 108 can be accessed when installed in intramedullary canal 202 of femur 204, even after femoral implant 212 has been installed on femur 204.

Because cap 108 is accessible when installed in intramedullary canal 202 and because cap 108 is removably threaded to secondary insert 104 (shown in FIG. 3, for example), cap 108 can be removed from secondary insert 104 when implantable sensor is installed in femoral intramedullary canal 202. In some examples, cap 108 can be removed from secondary insert 104 when implantable sensor 100 is installed in femoral intramedullary canal 202 and while femoral implant 212 is installed. By removing cap 108, sensor module 106 can also be removed to allow for replacement or repair of components, such as capacitor 128, without removal of the entirety of implantable sensor 100.

FIG. 6 also shows how optical fibers 143 pass through passageways 152 to reach an environment around the joint cavity and an environment generally surrounding the distal portion of femur 204. This way, optical fibers 143 can transmit optical information sensed from the environment near the distal area of femur 204, such as synovial fluid, to sensors within implantable sensor 100, such as first sensor 134, second sensor 135, and third sensor 136 (of FIGS. 3 and 4). In some examples, optical fibers 143 may not be included and passageways 152 can act as conduits for synovial fluid (or other fluid), drawing fluid through cap 108 for sensing.

In operation of some examples, optical fibers 143 can transmit to first sensor 134 an optical condition of the environment of the joint cavity or the environment around the distal termination of femur 204. First sensor 134 can then convert the optical condition into a sensor signal that can be correlated to Ph or glucose of the sensed environment. In some examples, second sensor 135 can produce a second sensor signal as a function of a second sensed condition. Second sensor 135 can also be connected to one or more optical fibers 143 for producing a second sensor signal that can be correlated to Ph or glucose of the sensed environment. In some examples, third sensor 136 can be a temperature sensor, such as a thermistor, for producing a third sensor signal as a function of the temperature around third sensor 136. Because implantable sensor 100 is implanted in intramedullary canal, the internal temperature of implantable sensor 100 can be similar to the temperature of the environment surrounding implantable sensor 100, such as the temperature of intramedullary canal 202, joint cavity, or the environment around the distal portion of femur 204. Any of first sensor 134, second sensor 135, and third sensor 136 can be configured similarly to any other of these sensors described above.

The sensor signals produced by first sensor 134, second sensor 135, and third sensor 136 can be transmitted from implantable sensor 100 (as described further below) to an external device that can be configured to determine whether or not an infection exists in the sampled environment. Not only can infections be harmful to a patient's health, infections can lead to repeated surgery and/or replacement of knee prostheses, sometimes called revision surgeries. By detecting early signs of infection, implantable sensor 100 can alert a patient and/or medical personnel to the existence of an infection, which can help to prevent worsening of infections and can therefore prevent future procedures, such as revisions, saving cost and improving quality of life.

Figure 7:
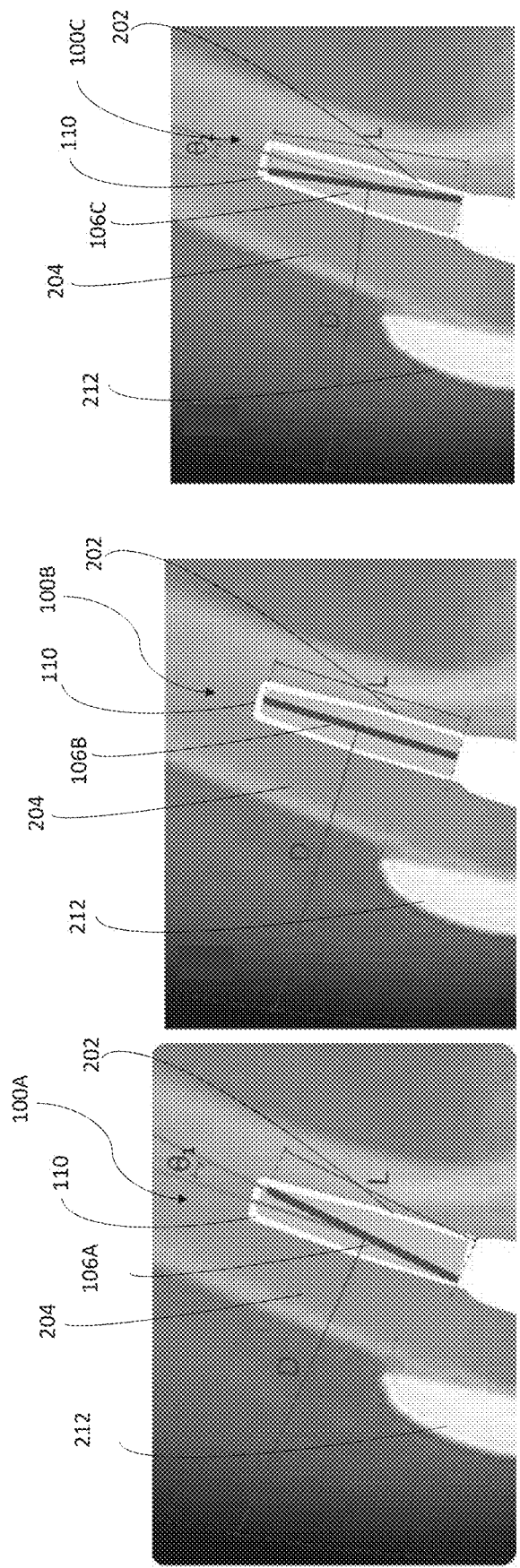
FIGS. 7A-7C illustrate an electromagnetic image of an implantable sensor installed in a femoral intramedullary canal with an antenna at multiple angles, in accordance with at least one example of this disclosure.

FIG. 7A illustrates implantable sensor 100A with antenna coil 118A installed in femoral intramedullary canal 202 of femur 204 at a first coil angle $\theta_1$. FIG. 7B illustrates implantable sensor 100B with antenna coil 118B installed in femoral intramedullary canal 202 of femur 204 at such that antenna coil 118B does not have a coil angle. FIG. 7C illustrates implantable sensor 100C with antenna coil 118C installed in femoral intramedullary canal 202 of femur 204 at a second coil angle $\theta_2$.

Wireless signals transmitted to and from antenna coils 106A-C can be affected by soft tissues, bones, and femoral implant 212. In one example, antenna coils 106A-106C can be optimized to transmit wireless signals by varying an angle of antenna coils 106A-106C. In some examples, such as the example shown in FIG. 6A, antenna coil 118A can be placed within proximal portion 110 at first coil angle $\theta_1$, which can be an angle of 1° through 90°, in some examples. In some other examples, first coil angle $\theta_1$ can be an angle between about 8° and about 10°, such as 9°.

In some examples, such as the example shown in FIG. 7B, antenna coil 118B can be placed within proximal portion 110 to have a coil angle of 0°. In some examples, such as the example shown in FIG. 7B, antenna coil 118C can be placed within proximal portion 110 at second coil angle $\theta_2$, which can be an angle of −1° through −90°, in some examples. In some other examples, first coil angle $\theta_1$ can be an angle between about −8° and about −10°, such as −9°.

Figure 8:
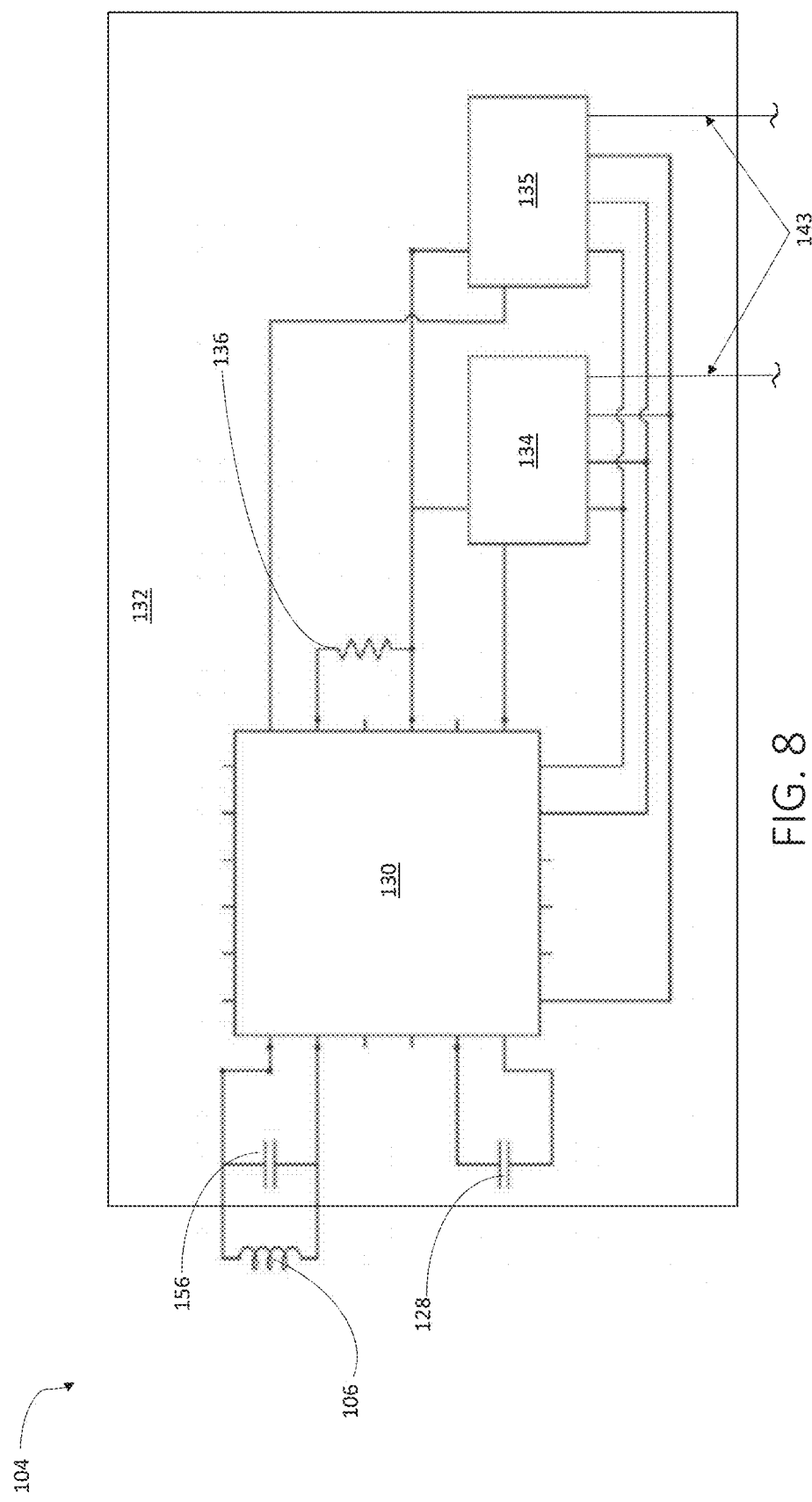
FIG. 8 illustrates a schematic of electrical components of an implantable sensor, in accordance with at least one example of this disclosure.

FIG. 8 illustrates a schematic of sensor module 104, which can include antenna coil 118, capacitor 128, communication chip 130, PCB 132, first sensor 134, second sensor 135, third sensor 136, optical fibers 143, and tuning capacitor 156.

Capacitor 128, communication chip 130, first sensor 134, second sensor 135, third sensor 136, and tuning capacitor 156 can be soldered to or otherwise coupled to PCB 132. PCB 132 can include a non-conductive substrate with an etched copper plate as a laminated layer that can provide the electrical connections of PCB 132.

Communication chip 130 can be a communication processor configured to receive inputs, process input, and produce output formatted for wireless transmission. For example, communication chip 130 can be a near field contact chip (NFC) including a low-power microcontroller.

In some examples, capacitor 128 can be configured to store power received from antenna coil 118, which can be distributed to power communication chip 130, which can then be distributed by communication chip 130 to other components of sensor module 104, as necessary. In some examples, capacitor 128 can be a replaceable battery, and the like, configured to provide power to communication chip 130, which can then be distributed by communication chip 130 to other components of sensor module 104, as necessary.

In some examples, tuning capacitor 156 can be connected in parallel to antenna coil 118 and electrically connected to communication chip 130. Tuning capacitor 156 can be used for radio frequency (RF) tuning of antenna coil 118 to optimize sending and receiving of wireless signals from and to antenna coil 118.

As shown in FIG. 8, first sensor 134 and second sensor 135 can be connected to receive power and control signals from communication chip 130. First sensor 134 and second sensor 135 can also be communicatively coupled to communication chip 130. In some examples, optical fibers 143 can connect directly to first sensor 134 and second sensor 135, as shown in FIG. 8. In some examples, optical fibers 143 can be other types of conductors, such as wires.

Third sensor 136 is shown as being a resistive temperature sensor, such as a thermistor, and the like. In some other examples, third sensor 136 can be configured similarly to first sensor 134 and second sensor 135.

In operation of one embodiment, sensor 100 can be inactive. Then, an external device can transmit power using induction to antenna coil 118, which can be distributed to communication chip 130 and then on to first sensor 134, second sensor 135, and third sensor 136. Thereafter, first sensor 134, second sensor 135, and third sensor 136 can be controlled to take individual measurements by communication chip 130, as may be instructed by the external device.

Then, communication chip 130 can receive a first sensor signal from first sensor 134, a second sensor signal from second sensor 135, and a third sensor signal from third sensor 136. Communication chip 130 can analyze and/or format the received sensor signals for wireless transmission via antenna coil 118. Because first sensor 134, second sensor 135, and third sensor 136 can be configured to produce sensor signals indicative of the presence of an infection in an environment surrounding implantable sensor 100, such as the environment of a human knee, sensor module 104 can enable implantable sensor 100 to transmit wireless signals via communication chip 130 and antenna coil 118 to an external device to help detect the existence of an infection.

To reduce power consumption, communication chip may send and receive signals to and from first sensor 134, second sensor 135, and third sensor 136 in predetermined time intervals. Similarly, communication chip can send and receive signals to and from antenna coil 118 in predetermined time intervals.

FIG. 9A illustrates an isometric view of secondary insert 104. FIG. 9B illustrates a plan view of secondary insert 104. FIG. 9C illustrates a proximal end view of secondary insert 104. FIG. 9D illustrates a distal end view of primary insert 104. FIG. 9E illustrates a cross-section view of secondary insert 104 across indicators 9E-9E of FIG. 9A. FIG. 9F illustrates a cross-section view of secondary insert 104 across indicators 9F-9F of FIG. 9E. FIGS. 9A-9F are discussed concurrently.

FIGS. 9A-9F are consistent with FIGS. 1, 3, and 4 discussed above, but show additional details of secondary insert 104, which can include snap fits 120 having projections 123, and can include coil connector 122, secondary insert bore 146, internal threaded portion 148, ribs 158, rib channels 160, and distal channels 162.

As shown in FIG. 9E, secondary insert bore 146 can extend from a distal end of secondary insert 104 towards and through a proximal end. Secondary insert bore 146 can have a diameter that varies. For example, a diameter of secondary insert bore 146 can be larger between the proximal and distal ends of secondary insert 104 to accommodate sensor module 106, as shown in FIGS. 3 and 4. Secondary insert bore 146 can be smaller at the proximal end of secondary insert 104 to provide a passage sized to secure coil connector 122. Further, secondary insert bore 146 can be smaller at the proximal end of secondary insert 104 to provide additional material thickness for snap fits 120. At the distal end of secondary insert 104, secondary insert bore 146 can include internal threaded portion 148 that can be configured to threadably engage threaded portion 142 of cap 108, as shown in FIGS. 3 and 4.

In some examples, secondary insert 104 can include ribs 158, which can extend axially along an outer surface of secondary insert 104 between the distal and proximal ends of secondary insert 104. As shown in FIG. 9E, ribs 158 can have be radial projections having a geometric shape similar to a triangular prism, in some examples, but can have other geometric shapes in some other examples. Ribs 158 can be placed around an entirety of the circumference of secondary insert 104, in some examples. In some other examples, ribs 158 can be interrupted by rib channels 160, as described further below. Ribs 158 can be spaced by angle A, as shown in FIG. 9F. Angle A can be an angle of about 5° to about 180° in some examples. In some examples, angle A can be an angle of about 10° to about 20° in other examples, such as 15°, for example. The geometric shape and spacing of ribs 158 can dictate a quantity of ribs 158 disposed around the circumference of secondary insert 104. In the example of FIG. 9F, the ribs can be spaced at 15°, except for where rib grooves create a larger space between ribs 158, such that 20 of ribs 158 are spaced around the circumference of secondary insert 104.

In operation of some examples, ribs 158 can engage with grooves of primary insert 102 (shown in later figures), to circumferentially secure secondary insert 104 within primary insert 102. In some examples, the consistent spacing between ribs 158 and the uniform geometry of ribs 158 can allow secondary insert 104 to be inserted and secured in primary insert 102 in a variety of positions, as discussed further below.

In some examples, secondary insert 104 can include rib channels 160, which can extend axially along an outer surface of secondary insert 104 between the distal and proximal ends. Rib channels 160 can be approximately the same length as ribs 158. In some examples, rib channels can be a space between ribs 158, and in some examples, rib channels 160 can be a groove or channel in the outer surface of secondary insert 104.

In some examples, secondary insert 104 can include distal channels 162, which can be a groove or channel formed in the outer surface of secondary insert 104 proximate the distal end. Distal channels 162 can have a quantity equal to the quantity of rib channels 160, and can be circumferentially aligned with rib channels 160. In operation of some examples, rib channels 160 and distal channels 162 can be configured to allow air to escape from primary insert 102 when secondary insert 104 is inserted into primary insert 102. This can prevent a pressure from building within primary insert 102 during installation of secondary insert 104.

FIG. 10A illustrates a plan view of primary insert 102, in accordance with at least one example of this disclosure. FIG. 10B illustrates a cross-section view of primary insert 102 across indicators 10B-10B of FIG. 10A, in accordance with at least one example of this disclosure. FIG. 10C illustrates a cross-section view of primary insert 102 across indicators 10C-10C of FIG. 10B, in accordance with at least one example of this disclosure. FIGS. 10A-10C are discussed concurrently.

FIGS. 10A-10C are consistent with FIGS. 1, 3, and 4 below, but show additional details of primary insert 102, which can include proximal portion 110, distal portion 112, proximal end 114, distal end 116, central bore 144, fins 164, distal opening 166, alignment grooves 168, and distal flange 170.

Central bore 144 can be a bore beginning at distal opening 166 proximate distal end 116 and extending through distal portion 112 and proximal portion 110, terminating in proximal portion 110 prior to proximal end 114. In some examples, central bore 144 can have a diameter in proximal portion 110 that is larger than a second diameter in distal portion 112.

Fins 164 can be radial projections extending axially along an outer surface of distal portion 112 of primary insert 102. Fins 164 can be circumferentially disposed around distal portion 112 and can include a quantity of fins 164 such as 1, 2, 3, 4, 5, 6, 10, 15, and the like. Fins 164 can be configured to engage an intramedullary canal of a femur, such as intramedullary canal 202 of FIG. 2, to prevent axial and rotational movement of primary insert 102 relative to intramedullary canal 202 and femur 204, for example.

Distal flange 170 can be integral to distal portion 112 and can be located at distal end 116. Distal flange 170 can have an outer diameter that is larger than a diameter of distal portion 112 and equal to an outer diametric dimension of fins 164. In operation of some examples, distal flange 170 can provide a mating surface for cap 108.

Alignment grooves 168 can be grooves formed in an inner surface of distal portion 112, that extend radially into central bore 144 and extend axially along bore 144 beginning proximate distal end 116 and terminating prior to proximal portion 110. Alignment grooves 168 can be spaced by angle B, as shown in FIG. 10C. Angle B can be an angle of about 5° to about 180° in some examples. In some examples, angle B can be an angle of about 10° to about 20° in other examples, such as 15°, for example.

The geometric shape and spacing of alignment grooves 168 can be designed to mate with ribs 158 of FIGS. 9A-9F. In this way, ribs 158 can be required to align with alignment grooves 168 for secondary insert 104 to be inserted into primary insert 102. Alignment grooves 168 can be configured to have a relatively tight fit with ribs 158 so that secondary insert 104 can be easily inserted into and removed from primary insert 102 while preventing secondary insert 104 from rotating relative to primary insert 102 while secondary insert 104 is within primary insert 102.

Because alignment grooves 168 are of the same shape and size as ribs 158, secondary insert 104 can be inserted into primary insert 102 in many orientations. In operation of some examples, the exposure of optical fibers 143 (of FIG. 3, for example) to synovial fluid around femur 204 (of FIG. 2, for example) can be improved by altering an orientation of secondary insert 104 relative to primary insert 102 during a procedure. That is, once cap 108 (of FIG. 3, for example) is secured to secondary insert 104, the position of optical fibers 143 are fixed relative to cap 108 and secondary insert 104. And, once primary insert 102 is installed into a femur, such as femur 204 (of FIG. 2, for example), a position of primary insert 102 is fixed relative to femur 204. Therefore, after primary insert 102 has been installed in intramedullary canal 102, secondary insert 104 can rotated to optimize exposure of optical fibers 143 to their surrounding environment, such as the joint cavity, which can improve sensor performance.

Figure 11C:
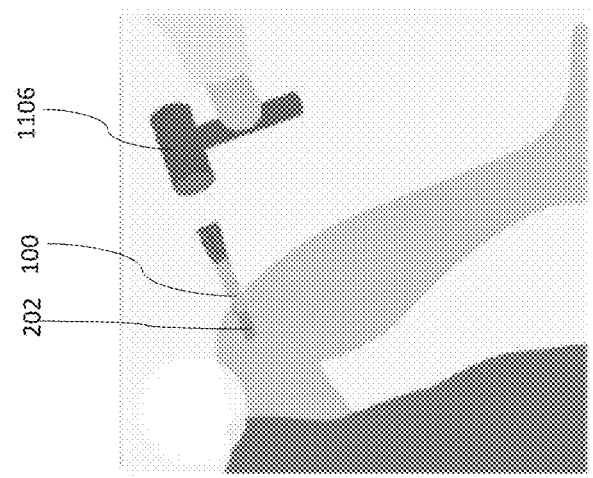
FIG. 11C illustrates a step of a surgical procedure, in accordance with at least one example of this disclosure.
Figure 11B:
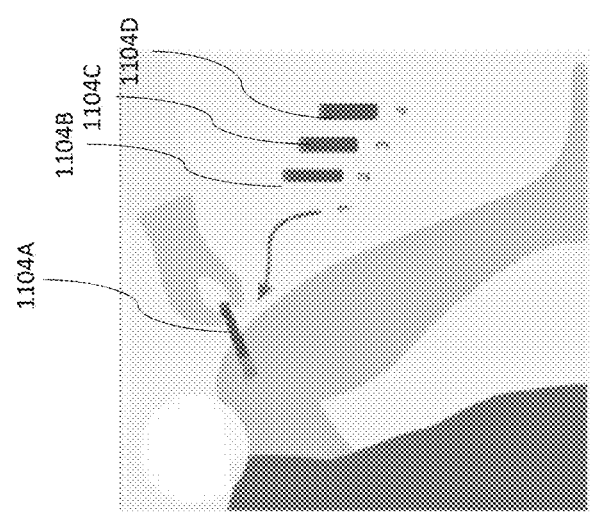
FIG. 11B illustrates a step of a surgical procedure, in accordance with at least one example of this disclosure.
Figure 11A:
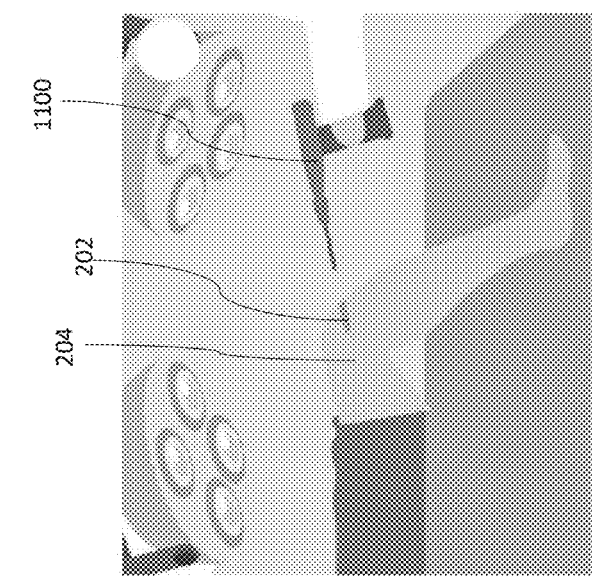
FIG. 11A illustrates a step of a surgical procedure, in accordance with at least one example of this disclosure.

FIGS. 11A-11C illustrate steps of a surgical procedure, in accordance with at least one example of this disclosure. In the step shown in FIG. 11A, a bore can be drilled using drill 1100 in intramedullary canal 202 of femur 204. In the step shown in FIG. 11B, each of trial rods 1104A-1104D can be inserted into the bore drilled in intramedullary canal 204 for the purpose of selecting a size of implantable sensor 100 that will have an appropriate fit within intramedullary canal 202. In the step shown in FIG. 11C, implantable sensor 100 having an appropriate size can be inserted into intramedullary canal 202, where mallet 1106 can be used to apply the force necessary to entirely insert and secure implantable sensor 100 into intramedullary canal 202 of femur 204.

Figure 12:
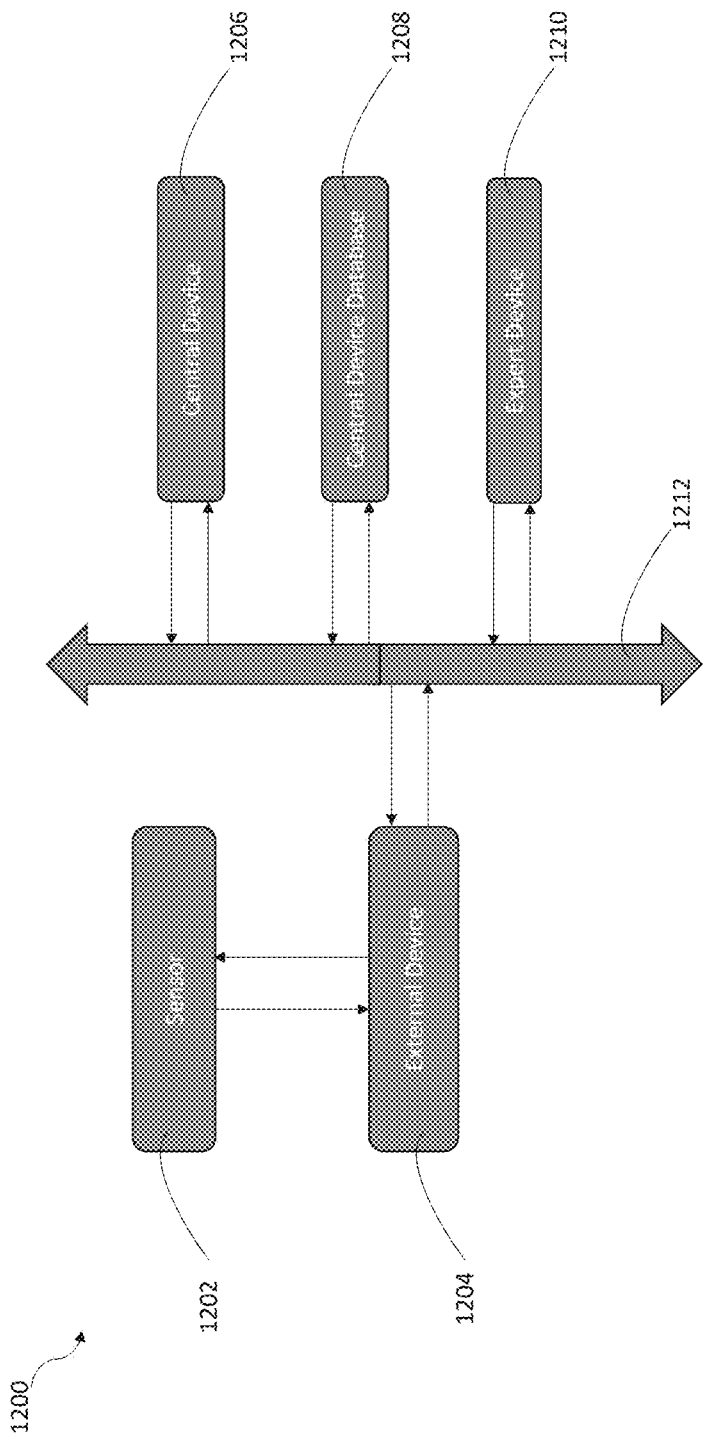
FIG. 12 illustrates a schematic components of a sensor system, in accordance with at least one example of this disclosure.

FIG. 12 illustrates a schematic of components of sensor system 1200, in accordance with at least one example of this disclosure. Sensor system 1200 includes sensor 1202, external device 1204, central device 1206, central device database 1208, expert device 1210, and connection medium 1212.

Sensor 1202 can be an implantable sensor consistent with FIGS. 1-10. External device 1204 can be a portable device, such as a handheld computer, for example, a smart phone, a tablet, a laptop with a connected sensor, or any other portable computing device including a processor and wireless communication capabilities. In yet other examples, expert device 1204 can include only transmitting and energy transmitting functionalities. Central device 1206 and expert device 1210 can be a portable device, as described above, or can be a stationary device or devices, such as a desktop computer or a central server system accessible through a program or online interface, such as a web page. Central device database 1208 can be a database for storing measurements and analysis from external device 1204, central device 1206, and expert device 1210. Central device database 1208, external device 1204, central device 1206, and expert device 1210 can include machine readable medium.

The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Connection medium 1212 can be a communication network utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi® or IEEE 802.15.4 family of standards known as ZigBee)), as the personal area network family of standards known as Bluetooth® that are promulgated by the Bluetooth Special Interest Group, peer-to-peer (P2P) networks, among others. Connection medium 1212 can also be a combination of networks.

Sensor 1202 can be in communication with external device 1204 through a wireless connection, such as Bluetooth, NFC, wi-fi, other electromagnetic based communication protocols, and the like. External device 1204, central device 1206, central device database 1208, and expert device 1210 can be in wireless or wired communication with connection medium 1212. Sensor system 1200 can operate as described in the FIGS. above, and in the method described below in FIG. 13.

Figure 13:
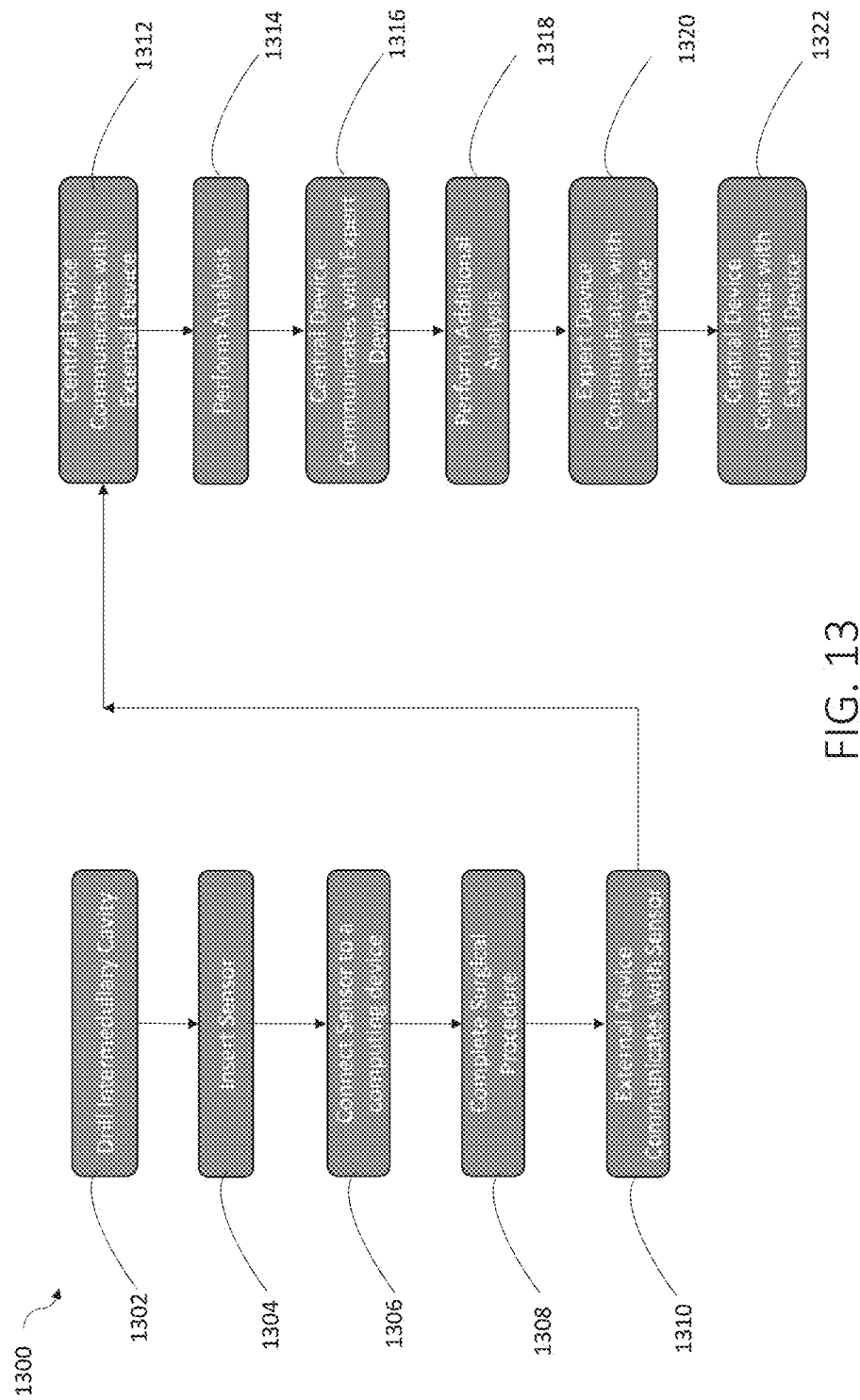
FIG. 13 illustrates a method of using a sensor system, in accordance with at least one example of this disclosure.

FIG. 13 illustrates a method 1300 of using sensor system 1200 of FIG. 12, in accordance with at least one example of this disclosure. The steps or operations of method 1300 are illustrated in a particular order for convenience and clarity; many of the discussed operations can be performed in a different sequence or in parallel without materially impacting other operations. Method 1300 as discussed includes operations performed by multiple different actors, devices, and/or systems. It is understood that subsets of the operations discussed in method 1300 attributable to a single actor, device, or system could be considered a separate standalone process or method. At step 1302, the method 1300 can begin with an intramedullary canal being drilled, so that an implantable sensor can be inserted into the intramedullary canal at step 1304. At step 1306, the method 1300 can continue with a computing device, such as external device 1204 of FIG. 12, connecting to the sensor. At this time, a communicative link can be confirmed and transmission of power and data can occur between the external device and sensor to functionally test the connection.

After completion of the surgical procedure at step 1308, the external device can distribute power to sensor 1202, enabling communication between the external device and sensor 1202, which is implanted into the patient. For example, sensor data, such as temperature, Ph, and glucose readings, can be transmitted from sensor 1202 to external device 1204. External device 1204 can perform analysis and then communicate with central device 1206 at step 1312. Central device 1206 can perform further analysis at step 1314, before communicating with expert device 1210 at step 1316. In some examples, analysis can be performed in external device 1204 at step 1310 prior to communication with central device 1206.

Analysis performed at steps 1314 and 1318 can include analyzing data from sensor 1202 to determine the presence of an infection. Other analysis such as determining remaining capacitor health, signal strength, and component functionality may also be performed. In some examples, where the device is battery-powered, wireless charging of the battery can be performed.

At step 1318 an expert may perform analysis outside of expert device 1210, which can then be entered into expert device 1210. Thereafter, expert device 1210 can then communicate with central device 1206 at step 1320 to relay any additional data and/or analysis performed at step 1318. Thereafter, all of the analysis and data derived from central device 1206, central device database 1208, and expert device 1210 can be communicated to external device 1204 at step 1322, where a user can view the data and analysis to make a decision regarding the joint in which sensor 1202 is installed, or can receive an instruction containing a decision.

This method offers the benefit of providing measurement data from within a joint containing a prosthesis that can be used to detect the presence of an infection. Moreover, the data can be sent to multiple devices, such as an external device, a central device, a central device database, and an expert device, to provide detailed and in-depth analysis on the data retrieved, such as comparing the data to data received from other sensors, and analysis performed by experts possessing knowledge not readily available, to determine the presence of an infection or other problem.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An implantable sensor configured to be inserted in an intramedullary canal, the implantable sensor comprising:
   a primary insert including a distal end, a proximal end opposite the distal end, and a central bore extending from an opening in the distal end towards the proximal end;
   a secondary insert receivable within the central bore through the opening, the secondary insert comprising:
      a body removably engageable with an inside surface of the central bore; and
      a sensor module disposable within the body and configured to produce a sensor signal as a function of a first sensed parameter indicative of infection;
   a cap releasably securable to the secondary insert, wherein the cap and sensor module are releasable from the secondary insert while the secondary insert is inserted in the intramedullary canal; and
   an antenna disposed in the central bore, the antenna configured to:
      transmit a wireless signal as a function of the sensor signal.

2. The implantable sensor of claim 1, wherein the implantable sensor comprises one of a temperature sensor, a pH sensor, an oxygen sensor, a carbon dioxide sensor, and a glucose sensor.

3. The implantable sensor of claim 1, wherein the antenna is configured to receive power from an external source and distribute the power to the sensor.

4. The implantable sensor of claim 1, wherein the cap further comprises:
   a plurality of arms projecting proximally from a proximalsurface of the cap and configured to retain the sensor module.

5. The implantable sensor of claim 1, wherein the secondary insert further comprises:
   a second sensor configured to produce a second sensor signal as a function of a second sensed parameter indicative of infection.

6. The implantable sensor of claim 5, wherein the secondary insert further comprises:
   a third sensor configured to produce a third sensor signal as a function of a third sensed parameter indicative of infection.

7. The implantable sensor of claim 1, wherein the secondary insert further comprises:
   an optical fiber connected to the sensor module and extending through a periphery of the secondary insert to expose the optical fiber to a joint cavity adjacent to the intramedullary canal to send an optical signal to the sensor module as a function of sensed optical conditions of the joint cavity.

8. The implantable sensor of claim 7, further comprising:
   a cap releasably securable to the secondary insert, the cap comprising:
   a passage exposing the sensor module to the joint cavity, the passage receivable of the optical fiber.

9. The implantable sensor of claim 1, wherein the central bore further comprises a plurality of grooves extending axially along a surface of the central bore, and wherein the secondary insert further comprises a plurality of ribs projecting radially outward from an outer surface of the secondary insert and extending axially along the outer surface, the plurality of ribs mateable with the plurality of grooves to prevent rotation of the secondary insert relative to the primary insert.

10. An implantable sensor configured to be inserted in an intramedullary canal, the implantable sensor comprising:
   a primary insert including a distal end, a proximal end opposite the distal end, and a central bore extending from an opening in the distal end towards the proximal end;
   a secondary insert receivable within the central bore through the opening, the secondary insert comprising:
      a body removably engageable with an inside surface of the central bore; and
      a sensor module disposable within the body and configured to produce a sensor signal as a function of a first sensed parameter indicative of infection;
   a cap releasably securable to the secondary insert, the cap including a plurality of arms projecting proximally from a proximal surface of the cap and configured to retain the sensor module; and
   an antenna disposed in the central bore, the antenna configured to transmit a wireless signal as a function of the sensor signal.

11. The implantable sensor of claim 10, wherein the cap and sensor module are releasable from the secondary insert while the secondary insert is inserted in the intramedullary canal.

12. The implantable sensor of claim 10, wherein the central bore further comprises a plurality of grooves extending axially along a surface of the central bore, and wherein the secondary insert further comprises a plurality of ribs projecting radially outward from an outer surface of the secondary insert and extending axially along the outer surface, the plurality of ribs mateable with the plurality of grooves to prevent rotation of the secondary insert relative to the primary insert.

13. An implantable sensor configured to be inserted in an intramedullary canal, the implantable sensor comprising:
   a primary insert including a distal end, a proximal end opposite the distal end, and a central bore extending from an opening in the distal end towards the proximal end; and
   a secondary insert receivable within the central bore through the opening, the secondary insert comprising:
   a body removably engageable with an inside surface of the central bore;
   a sensor module disposable within the body and configured to produce a sensor signal as a function of a first sensed parameter indicative of infection; and
   an optical fiber connected to the sensor module and extending through a periphery of the secondary insert to expose the optical fiber to a joint cavity adjacent to the intramedullary canal to send an optical signal to the sensor module as a function of sensed optical conditions of the joint cavity.

14. The implantable sensor of claim 13, further comprising:
   a cap releasably securable to the secondary insert, the cap comprising:
   a passage exposing the sensor module to the joint cavity, the passage receivable of the optical fiber.

15. The implantable sensor of claim 13, further comprising:
   an antenna disposed in the central bore, the antenna configured to transmit a wireless signal as a function of the sensor signal.

* * * * *

UNITED STATES PATENT AND TRADEMARK OFFICE
CERTIFICATE OF CORRECTION

PATENT NO. : 10,898,106 B2  
APPLICATION NO. : 15/399131  
DATED : January 26, 2021  
INVENTOR(S) : Bodewes et al.

Page 1 of 1

It is certified that error appears in the above-identified patent and that said Letters Patent is hereby corrected as shown below:

In the Claims

In Column 18, Lines 12-13, in Claim 4, delete "proximalsurface" and insert --proximal-surface-- therefor Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*